(12) United States Patent
Eder et al.

(10) Patent No.: US 7,160,917 B2
(45) Date of Patent: Jan. 9, 2007

(54) SPIROBENZOFURAN LACTAMS AND THEIR DERIVATIVES, PROCESSES FOR THEIR PREPARATION AND USE THEREOF

(75) Inventors: Claudia Eder, Hofheim (DE); Michael Kurz, Hofheim (DE); Luigi Toti, Hochheim (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 118 days.

(21) Appl. No.: 10/732,702

(22) Filed: Dec. 10, 2003

(65) Prior Publication Data

US 2004/0138280 A1   Jul. 15, 2004

Related U.S. Application Data

(60) Provisional application No. 60/465,999, filed on Apr. 28, 2003.

(30) Foreign Application Priority Data

Dec. 13, 2002 (DE) ................................ 102 58 650

(51) Int. Cl.
  *A61K 31/4035* (2006.01)
  *C07D 209/44* (2006.01)
(52) U.S. Cl. ................... 514/416; 548/469; 548/470; 548/472
(58) Field of Classification Search ............. 548/469, 548/470, 472; 514/416, 418
  See application file for complete search history.

(56) References Cited

U.S. PATENT DOCUMENTS

| 5,366,986 A | 11/1994 | Sindelar et al. |
| 6,627,604 B1 | 9/2003 | Vertesy |

FOREIGN PATENT DOCUMENTS

GB   1420528   1/1976

OTHER PUBLICATIONS

Sakai et al (1998): STN International CAPLUS database, Columbus (Ohio), accession No.,1998: 627183.*
Deng, et al., Total Synthesis and Structure Revision of *Stachybotrys spirolactams*, J. of Org. Chem.; 68; 2003; pp. 7422-7427.
Eppley, et al., Structures of Satratoxin F and Satratoxin G, Metabolites of *Stachybotrys atra*, J. of Org. Chem.; 45; 1980; pp. 2522-2523.
Kende, et al., Enantioselective Total Synthesis and Structure Revision of Spirohydrobenzofuranlactam 1. Total Sythesis of Stachybotrylactam, Organic Letters; 5(10; 2003; pp. 1785-1788.
Roggo, et al., Novel Spirohydrobenzofuranlactams as Antagonists of Endothelin and as Inhibitors of HIV-1 Protease Produced by *Stachybotrys* sp., J. of Antibiotics.; 49(4); 1996; pp. 374-379.
Brock T.D., et al., Microbial Genetics, Chapter 7., Biology of Microorganisms; Seventh Edition; Prentice Hall; 1994; pp. 238-247.
Charlton P., The Status of Plasminogen Acivator Inhibitor-1 as a Therapeutic Target, Expert Opinion on Investigational Drugs; vol. 6; No. 5; 1997; pp. 539-554.
Dawson S., et al., The Status of PAI-1 as a Risk Factor For Arterial and Thrombotic Disease: A Review, Atherosclerosis; vol. 95; 1992; pp. 105-117.
Declerck P.J., et al., Minisymposium: The Role of the Fibrinolytic System in the Pathophysiology and Treatment of Thrombosis, J. Internal Medicine; vol. 236; 1994; pp. 425-432.
Frankenne F., et al, Molecular Interactions Involving Urokinase Plasminogen Activator (uPA), Its Receptor (uPAR) and Its Inhibitor, Plasminogen Activator Inhibitor-1 (PAI-1), As New Targets For Tumour Therapy, Emerging Therapeutic Targets; vol. 3; No. 3; 1999; pp. 469-481.
Stolp H., Dispersal of Microorganisms and Development of Microbial Populations., Microbial Ecology Organisms, Habitats, Activities, Chapter 6.; Cambridge University Press; 1988; pp. 172-180.
Vassalli J.D., et al, The Plasminogen Activator/Plasmin System, J. Clin. Invest; vol. 88; Oct. 1991; pp. 1067-1072.
Vertesy L., et al., Memnopeptide A, a Novel Terpene Peptide From Memnoniella With an Activating Effect On SERCA2, Journal Of Antibiotics; vol. 54; No. 10; Oct. 2001; pp. 771-782.
Salt Formation, Chapter 76, Remington Pharmaceutical Sciences; 17th Edition; 1985; p. 1418.

* cited by examiner

*Primary Examiner*—Golam M. M. Shameem
(74) *Attorney, Agent, or Firm*—Ronald G. Ort; Jiang Lin

(57) ABSTRACT

The present invention relates to spirobenzofuran lactam derivatives of the formula I

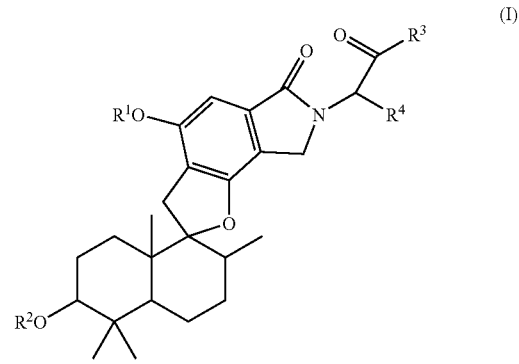

which are formed during fermentation by the microorganism *Stachybotris atra* ST002348, DSM 14952, processes for their preparation, their use as pharmaceuticals, and the microorganism *Stachybotris atra* ST002348, DSM 14952.

6 Claims, No Drawings

SPIROBENZOFURAN LACTAMS AND THEIR DERIVATIVES, PROCESSES FOR THEIR PREPARATION AND USE THEREOF

This application claims the benefit of U.S. Provisional Application No. 60/465,999, filed Apr. 28, 2003, and incorporated herein by reference.

The present invention relates to novel active compounds (spirobenzofuran lactam derivatives), which are formed during fermentation by the microorganism *Stachybotris atra* ST002348, DSM 14952, processes for their preparation, their use as pharmaceuticals, pharmaceuticals containing spirobenzofuran lactam derivatives and the microorganism *Stachybotris atra* ST002348, DSM 14952.

The plasminogen activation system comprises an enzyme cascade which makes possible the controlled, localized formation of the proteolytic enzyme plasmin. The formation of plasmin plays an important role in a multiplicity of physiological and pathophysiological processes. Within this enzyme cascade, the conversion of the zymogen plasminogen into the proteolytically active plasmin is activated either by tPA (tissue type plasminogen activator) or uPA (urokinase type plasminogen activator). The plasmin activity can be controlled or regulated at different levels. The activity of tPA and uPA is in turn controlled by PAI-1 and PAI-2. While tPA is the most important plasminogen activator in fibrinolysis, uPA plays an important role in plasmin formation at sites where a degradation of extracellular matrix takes place. While uPA is regulated both by PAI-1 (plasminogen activator inhibitor 1) and PAI-2, there are indications that tPA is influenced only by PAI-1. PAI-1 thus plays an important role in the maintenance of the equilibrium between fibrin formation and fibrinolysis (J. D. Vassalli et al., J. Clin. Invest., 1991, 88, 1067–1072). Many studies yielded information that an increased PAI-1 level is a risk factor for cardiovascular diseases. Elevated PAI-1 concentrations were detected, inter alia, in the case of coronary heart disease, acute myocardial infarct, unstable angina pectoris, venous thrombosis and venous thromboembolisms (P. J. Declerck et al., J. Intern. Med., 1994, 236, 425–432; H. A. Dawsons, Atherosclerosis, 1992, 95, 105–117). These clinical studies point to the fact that PAI-1 is a novel target for the treatment of diseases which accompany decreased fibrinolysis, for example decreased wound healing (Charlton P., Exp. Opin. Invest. Drugs, 1997, 6, 539–554).

Elevated PAI-1 values are also connected with arterial thrombosis, arteriosclerosis, insulin resistance and macrovascular injuries in type II diabetes mellitus patients, hypoxia, septic shock, pneumonia and pulmonary fibrosis, and moreover with cancers, in particular breast cancer, intestinal cancer, gastric cancer, hepatic cancer, brain tumors, ovarian tumors, esophageal cancer, renal cancer, muscle cell carcinoma, in particular head and neck muscle carcinoma, PAI-1 being credited with a key role in the progress and the metastasis of cancers, in particular in the proteolysis, adhesion, mobilization, invasion, chemotaxis, proliferation and angiogenesis (P. Carlton, Exp. Opin. Invest. Drugs, (1997), 6(5), 539–554; F. Frankenne et al., Expert Opinion on Therapeutic Targets, 1999, 3(3), 469–481). A treatment of the diseases mentioned by way of introduction is therefore possible by inhibition of PAI-1.

It is therefore the object of the present invention to make available inhibitors of the plasminogen activator inhibitor 1 (PAI-1).

It has surprisingly being found that the microorganism strain *Stachybotris atra* ST002348, DSM 14952, is able to form compounds which effectively inhibit the plasminogen activator inhibitor 1 (PAI-1) in very low concentrations. The compounds of the formula (I) inhibit the inhibition of the enzymatic activity of tPA by PAI-1 and are accordingly suitable for the treatment and/or prophylaxis of coronary heart disease, acute myocardial infarct, unstable angina pectoris, venous thrombosis and venous thromboembolisms, arterial thrombosis, arteriosclerosis, insulin resistance and macrovascular injuries in type II diabetes mellitus patients, hypoxia, septic shock, pneumonia and pulmonary fibrosis, and cancers, in particular breast cancer, intestinal cancer, gastric cancer, hepatic cancer, brain tumors, ovarian tumors, esophageal cancer, renal cancer, muscle cell carcinoma, in particular head and neck muscle carcinoma. In particular, the compounds according to the invention are suitable for an antithrombotic therapy for treatment and prophylaxis in patients with coronary heart diseases and antithrombotic diseases of the peripheral venous system.

The invention thus relates to compounds of the formula (I), also called spirobenzofuran lactam derivatives below,

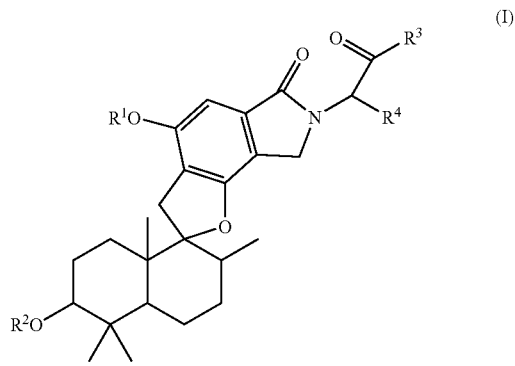

where;

$R^1$ and $R^2$ independently of one another are H, $C_1$–$C_6$-alkyl, $C_2$–$C_6$-alkenyl, $C_2$–$C_6$-alkynyl or $C_5$–$C_{14}$-aryl, in which alkyl, alkenyl, alkynyl and aryl are unsubstituted or mono- to trisubstituted by a radical from the group consisting of —OH, =O, —O—$C_1$–$C_6$-alkyl, —O—$C_2$–$C_6$-alkenyl, —O—$C_5$–$C_{14}$-aryl, —NH—$C_1$–$C_6$-alkyl, —NH—$C_2$–$C_6$-alkenyl, —NH[—C(=O)—($C_1$–$C_6$-alkyl)], —NH[—C(=O)—($C_5$–$C_{14}$-aryl)], —NH$_2$ or halogen, $R^3$ is —OH, —O—$R^1$ or —NH—$R^1$, and $R^4$ is H, $C_1$–$C_6$-alkyl, $C_2$–$C_6$-alkenyl, $C_5$–$C_{14}$-aryl or —($C_1$–$C_6$-alkyl)-($C_5$–$C_{14}$-aryl), and their physiologically tolerable salts and/or obvious chemical equivalents.

Preferably, $R^1$ and $R^2$ independently of one another are H or $C_1$–$C_6$-alkyl, particularly preferably H, $R^3$ is OH or —O—$C_1$–$C_6$-alkyl, particularly preferably OH, and $R^4$ is $C_1$–$C_6$-alkyl or —($C_1$–$C_6$-alkyl)-($C_5$–$C_{14}$-aryl), particularly preferably benzyl, 2-butyl or 1-(2-methylpropyl).

A compound of the formula (I) is particularly preferred where $R^1$ and $R^2$ are H, $R^3$ is OH and $R^4$ has the above-mentioned general or preferred meaning.

The invention further preferably relates to a compound of the formula (I) characterized by a compound of the formula (II),

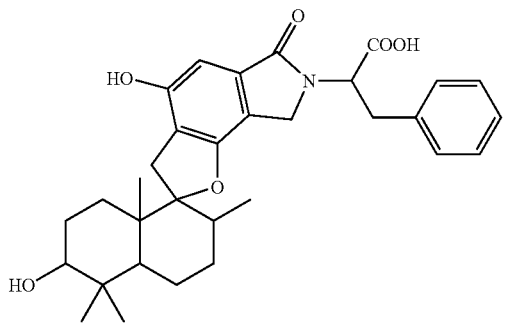

a compound of the formula (III) or

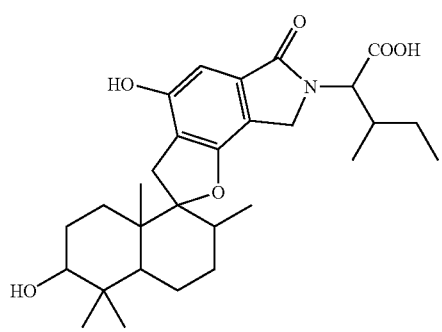

a compound of the formula (IV)

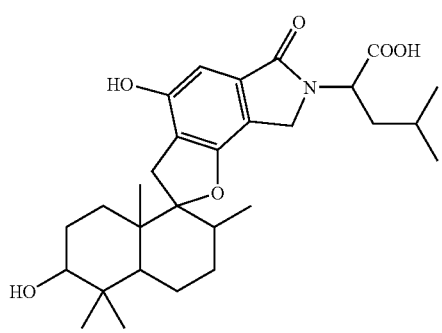

or a physiologically tolerable salt thereof.

Chiral centers in the compounds of the formula (I), (II), (III) and (IV) can, unless stated otherwise, be present in the R or in the S configuration. The invention relates both to the optically pure compounds and stereoisomer mixtures such as enantiomer mixtures and diastereomer mixtures.

$C_1$–$C_6$-alkyl is a straight-chain or branched alkyl having 1 to 6 C atoms, preferably having 1 to 4 C atoms, e.g. methyl, ethyl, i-propyl, tert-butyl and hexyl.

$C_2$–$C_6$-alkenyl is a straight-chain or branched alkenyl having 2 to 6 C atoms, which is mono-, di- or triunsaturated, e.g. allyl, crotyl, 1-propenyl, penta-1,3-dienyl and pentenyl.

$C_2$–$C_6$-alkynyl is a straight-chain or branched alkynyl having 2 to 6 C atoms, which is mono- or diunsaturated, e.g. propynyl, butynyl and pentynyl.

$C_5$–$C_{14}$-aryl is an aryl group having 5 to 14 C atoms, e.g. phenyl, benzyl or 1- or 2-naphthyl, which are substituted or unsubstituted by one, two or three substituents from the group consisting of halogen, e.g. chlorine, bromine, fluorine, $C_1$–$C_4$-alkyl, e.g. methyl, hydroxyl, $C_1$–$C_4$-alkoxy, e.g. methoxy or by trifluoromethyl.

Halogen is an element from the group consisting of fluorine, chlorine, bromine and iodine.

The invention further relates to a process for the preparation of a compound of the formula (I), which comprises fermenting the strain *Stachybotris atra* ST002348, DSM 14952, or one of its variants or mutants under suitable conditions in a culture medium until one or more of the compounds of the formula (I) accumulate in the culture medium and then isolating it from the culture medium and optionally converting it into chemical equivalents and/or a physiologically tolerable salt.

Preferably, the strain *Stachybotris atra* ST002348, DSM 14952, its mutants and/or variants is fermented in a nutrient solution or a solid medium (also called culture medium) having a carbon and nitrogen source and the customary inorganic salts until the compounds according to the invention accumulate in the culture medium, then the compounds are isolated from the culture medium and optionally separated into the individual active components.

The process according to the invention can be employed for fermentation on the laboratory scale (milliliter to liter range) and for the industrial scale (cubic meter scale).

A heavily producing colony of *Stachybotris atra* was proliferated in a preculture. The strain was deposited in the Deutsche Sammlung von Microorganismen und Zellkulturen GmbH, Mascheroder Weg 1B, 3300 Brunswick, Germany, according to the rules of the Budapest convention on Apr. 23, 2002 under the number DSM 14952 or the reference ST002348 of Aventis Pharma Deutschland GmbH allocated by the depositor.

On malt agar, *Stachybotris atra* ST002348, DSM 14952, has a white to orange-colored mycelium. The strain forms hyaline ellipsoid tubercular conidia (8–11×6–11 μm) characteristic of the species.

Instead of the strain *Stachybotris atra* ST002348, DSM 14952, it is also possible to employ its mutants and variants which synthesize one or more of the compounds according to the invention.

A mutant is a microorganism in which one or more genes of the genome have been modified, the gene or genes which are responsible for the ability of the organism to produce the inventive compound being retained functionally and hereditarily.

Such mutants can be produced in a manner known per se by physical means, for example irradiation, such as with ultraviolet rays or X-rays, or chemical mutagens, such as, for example, ethyl methanesulfonate (EMS); 2-hydroxy-4-methoxybenzophenone (MOB) or N-methyl-N'-nitro-N-nitroso-guanidine (MMNG), or as described by Brock et al. in "Biology of Microorganisms", Prentice-Hall, pages 238–247 (1984).

A variant is a phenotype of the microorganism. Microorganisms have the ability to adapt to their environment and therefore show marked physiological flexibility. In the case of phenotypic adaptation, all cells of the microorganism are involved, the nature of the alteration not being genetically conditioned and being reversible under altered conditions (H. Stolp, Microbial ecology: organisms, habitats, activities. Cambridge University Press, Cambridge, GB, page 180, 1988).

The screening for mutants and variants which synthesize one or more of the compounds according to the invention is carried out according to the following scheme:

preparation of mutants and/or variants according to methods known per se;

culturing of the mutants and/or variants obtained in this way;

lyophilization of the shaker cultures;

extraction of the lyophilizates using an organic solvent;

extraction of the compound from the culture filtrate using solid phases;

analysis by means of HPLC, TLC or by testing the biological activity;

optionally elucidation of the taxonomy of the mutants and/or variants.

The fermentation conditions described below apply for Stachybotris atra ST002348, DSM 14952, and mutants and variants thereof.

In a nutrient solution which contains a carbon source and a nitrogen source and the customary inorganic salts, Stachybotris atra ST002348, DSM 14952 produces the spirobenzofuran lactam derivatives.

Suitable preferred carbon sources for the aerobic fermentation are assimilable carbohydrates and sugar alcohols, such as glucose, lactose, sucrose or D-mannitol, and carbohydrate-containing natural products, such as, for example, malt extract or starch. Possible nitrogen-containing nutrients are: amino acids; peptides; proteins; degradation products of proteins and peptides, in particular peptides obtained synthetically or biosynthetically, for example casein, peptones or tryptones; meat extracts; yeast extracts; ground seeds, for example of corn, wheat, beans, soybeans or the cotton plant; distillation residues of alcohol production; meat meals or yeast extracts; ammonium salts; nitrates. Customary inorganic salts are, for example, chlorides, carbonates, sulfates or phosphates of an alkali metal or alkaline earth metal, of iron, zinc, cobalt or manganese.

The formation of the compounds according to the invention proceeds particularly readily in a nutrient solution which contains approximately 0.1 to 5%, preferably 0.5 to 2%, of starch, 0.2 to 5%, preferably 0.5 to 1%, of yeast extract and 0.2 to 5%, preferably 0.5 to 2%, of glucose. The data in percent are in each case based on the weight of the total nutrient solution.

In this nutrient solution, *Stachybotris atra* ST002348, DSM 14952, forms a mixture of spirobenzofuran lactam derivatives. Depending on the composition of the nutrient solution, the quantitative proportion of one or more of the spirobenzofuran lactam derivatives according to the invention can vary.

The microorganism is cultured aerobically, i.e., for example, submersed with shaking or stirring in shaker flasks or fermenters, optionally with introduction of air or oxygen. It can be carried out in a temperature range from approximately 18 to 35° C., preferably at approximately 20 to 30° C., in particular at 22 to 27° C. The pH range should be between 4 and 8, preferably between 5 and 6. The microorganism is in general cultured under these conditions for a period of 48 to 200 hours, preferably 72 to 168 hours.

Advantageously, the culturing is carried out in a number of stages, i.e. first one or more precultures are prepared in a liquid nutrient medium, and are then inoculated into the actual production medium, the main culture, for example in the volume ratio 1:10 to 1:100. The preculture is obtained, for example, by inoculating a mycelium into a nutrient solution and allowing it to grow for approximately 36 to 120 hours, preferably 48 to 72 hours. The mycelium can be obtained, for example, by allowing the strain to grow for approximately 3 to 21 days, preferably 4 to 10 days, on a solid or liquid nutrient medium, for example malt-yeast agar or potato-dextrose agar.

The course of the fermentation can be monitored by means of the pH of the cultures or of the mycelium volume and by chromatographic methods, such as, for example, high-performance liquid chromatography (HPLC), or testing the biological activity.

The isolation process described below serves for the purification of the spirobenzofuran lactam derivatives of the formula (I) according to the invention:

The isolation or purification of a spirobenzofuran lactam derivative according to the invention from the culture medium is carried out according to known methods taking into account the chemical, physical and biological properties of the natural substances. To test the concentration of the respective spirobenzofuran lactam derivatives in the culture medium or in the individual isolation stages, HPLC can be used, the amount of the substance formed expediently being compared with a calibration solution.

For isolation, the culture broth or the culture together with the solid medium are lyophilized, then the spirobenzofuran lactam derivatives are extracted from the lyophilizate using an organic solvent which is optionally miscible with water. The organic solvent phase contains the natural substances according to the invention; it is optionally concentrated in vacuo and further purified.

The further purification of one or more compounds according to the invention is carried out by chromatography on suitable materials, preferably, for example, on molecular sieves, on silica gel, alumina, on ion exchangers or on adsorber resins or on reversed phases (RP). With the aid of this chromatography, the spirobenzofuran lactam derivatives are separated. The chromatography of the spirobenzofuran lactam derivatives is carried out using buffered aqueous solutions or mixtures of aqueous and organic solutions.

Mixtures of aqueous or organic solutions are understood as meaning all organic solvents miscible with water, preferably methanol, 2-propanol and acetonitrile, in a concentration of 5 to 80% of solvent, preferably 20 to 50% of solvent or else any buffered aqueous solutions which are miscible with the organic solvents. The buffers to be used are the same as indicated above.

The separation of the spirobenzofuran lactam derivatives on the basis of their differing polarity is carried out with the aid of reversed phase chromatography, for example on MCI® (adsorber resin from Mitsubishi, Japan) or Amberlite XAD® (TOSOHAAS), or on further hydrophobic materials, such as, for example, on RP-8 or RP-18 phases. Moreover, the separation can be carried out with the aid of normal phase chromatography, for example on silica gel, alumina and the like.

The chromatography of the spirobenzofuran lactam derivatives is carried out using buffered or acidified aqueous solutions or mixtures of aqueous solutions with alcohols or other water-miscible organic solvents. The organic solvent used is preferably 2-propanol and acetonitrile.

Buffered or acidified aqueous solutions are understood as meaning, for example, water, phosphate buffer, ammonium acetate, citrate buffer in a concentration of up to 0.5 M and formic acid, acetic acid, trifluoroacetic acid or all commercially available acids known to the person skilled in the art, preferably in a concentration of up to 1%. In the case of buffered aqueous solutions, 0.1% ammonium acetate is particularly preferred.

Chromatography was carried out using a gradient which begins with 100% water and ends with 100% solvent; a linear gradient of 20 to 100% of 2-propanol or acetonitrile was preferably used.

Alternatively, gel chromatography or chromatography on hydrophobic phases can also be carried out. Gel chromatography is carried out on polyacrylamide or copolymer gels, such as, for example, Biogel-P 2® (Biorad) or Fractogel TSK HW 40® (Merck, Germany or Toso Haas, USA). The sequence of the aforementioned chromatographies is reversible.

The present invention furthermore relates to all obvious chemical equivalents of the compounds of the formula (I) according to the invention. Such equivalents are compounds which exhibit a slight chemical difference, i.e. have the same action or are converted into the compounds according to the invention under mild conditions. The equivalents mentioned also include, for example, salts, reduction products, oxidation products, esters, ethers, acetals or amides of the compounds of the formula (I) and equivalents which the person skilled in the art can prepare using standard methods, moreover all optical antipodes, diastereomers and stereomeric forms.

Physiologically tolerable salts of compounds of the formula (I) are understood as meaning both their organic and inorganic salts, as described in Remington's Pharmaceutical Sciences (17th edition, page 1418 (1985)). On account of the physical and chemical stability and the solubility, for acidic groups, inter alia, sodium, potassium, calcium and ammonium salts are preferred; for basic groups, inter alia, salts of hydrochloric acid, sulfuric acid, phosphoric acid or of carboxylic acids or sulfonic acids, such as, for example, acetic acid, citric acid, benzoic acid, maleic acid, fumaric acid, tartaric acid and p-toluenesulfonic acid are preferred.

Esters, ethers, amides and acetals can be prepared by methods described in the literature, e.g. in Advanced Organic Synthesis, 4th Edition, J. March, John Wiley & Sons, 1992 or Protective Groups in Organic Synthesis 3rd Edition, T. W. Green & P. G. M. Wuts, John Wiley & Sons, 1999.

The carboxyl group can be reduced to the alcohol, for example, using $LiAlH_4$ or esterified with the addition of catalytic amounts of an inorganic acid (for example $H_2SO_4$ or HCl). The hydroxyl groups can be etherified, for example, under the conditions of the Williamson ether synthesis.

For the detection of the inhibitors of PAI-1, a test is run in which the activation of a specific substrate by tPA is measured in the presence of a defined amount of PAI-1 and the substance in each case to be investigated. tPA is inhibited by PAI-1. An inhibition of PAI-1 results in an increased tPA activity. The enzymatic activity of tPA is measured colorimetrically by employing a chromogenic substrate which becomes colored after amidolysis.

$IC_{50}$ values for the spirobenzofuran lactam derivatives are indicated in table 1:

|  | $IC_{50}$ |
|---|---|
| Compound of the formula (II) | 41 µM |
| Compound of the formula (III) | 66 µM |
| Compound of the formula (IV) | 35 µM |

As inhibitors of PAI-1, the compounds according to the invention can be used for the treatment and/or prophylaxis of the diseases mentioned by way of introduction.

The invention therefore further relates to the use of a compound of the formula (I) according to the invention or of a physiologically tolerable salt thereof as a pharmaceutical in human or veterinary medicine or for the production of a pharmaceutical in human or veterinary medicine, in particular for the treatment and/or prophylaxis of coronary heart disease, acute myocardial infarct, unstable angina pectoris, venous thrombosis and venous thromboembolisms, arterial thrombosis, arteriosclerosis, insulin resistance and macrovascular injuries in type II diabetes mellitus patients, hypoxia, septic shock, pneumonia and pulmonary fibrosis, and cancers, in particular breast cancer, intestinal cancer, gastric cancer, hepatic cancer, brain tumors, ovarian tumors, esophageal cancer, renal cancer, muscle cell carcinoma, in particular head and neck muscle carcinoma, particularly preferably a pharmaceutical for the inhibition of clotting for the treatment of and/or as a prophylaxis for thromboembolic diseases.

In addition, the present invention relates to a pharmaceutical containing at least one compound of the formula (I), it being possible in principle for the compound or the compounds of the formula (I) to be administered as such alone or preferably as a mixture with one or more of the customary pharmacologically suitable vehicles or excipients.

The compounds according to the invention are stable in the solid state and in solutions in the pH range between 3 and 8, in particular 5 and 7, and can thus be incorporated into customary pharmaceutical preparations.

The pharmaceuticals according to the invention are in general administered orally or parenterally, but rectal administration is also possible in principle. Suitable solid or liquid pharmaceutical preparations forms are, for example, granules, powders, tablets, coated tablets, (micro)capsules, suppositories, syrups, emulsions, suspensions, aerosols, drops or injectable solutions in ampule form and preparations having a protracted release of active compound, in whose preparation vehicles and additives and/or excipients such as disintegrants, binders, coating agents, swelling agents, glidants or lubricants, flavorings, sweeteners or solubilizers are used.

Customary pharmacologically suitable vehicles or excipients are, for example, magnesium carbonate, titanium dioxide, lactose, mannitol and other sugars, talc, milk protein, gelatin, starch, vitamins, cellulose and its derivatives, animal or vegetable oils, polyethylene glycols and solvents, such as, for example, sterile water, alcohols, glycerol and polyhydric alcohols.

Optionally, the dose units for oral administration can be microencapsulated in order to delay the release or to extend it over a longer period of time, such as, for example, by coating or embedding the active compound in particle form in suitable polymers, waxes or the like.

Preferably, the pharmaceutical preparations are prepared and administered in the dose units, each unit containing as active constituent a specific dose of one or more compounds of the spirobenzofuran lactam derivatives according to the invention. In the case of solid dose units such as tablets, capsules and suppositories, this dose can be up to approximately 500 mg, but preferably approximately 0.1 to 200 mg, and in the case of injection solutions in ampule form up to approximately 200 mg, but preferably approximately 0.5 to 100 mg, per day.

The daily dose to be administered is dependent on the body weight, age, gender and condition of the mammal. Under certain circumstances, however, higher or lower daily doses may also be appropriate. The administration of the daily dose can be carried out both by single administration in the form of an individual dose unit or else in a number of smaller dose units and by multiple administration of subdivided doses at specific intervals.

The pharmaceuticals according to the invention are prepared by bringing one or more of the compounds of the formula (I) according to the invention, optionally with one or more of the customary vehicles or excipients, into a suitable administration form.

The invention is illustrated further in the following examples. Percentages relate to the weight. Mixing ratios in the case of liquids relate to the volume, unless stated otherwise.

EXAMPLE 1

Preparation of a Glycerol Culture of *Stachybotris atra* ST002348, DSM 14952

100 ml of nutrient solution (malt extract 2.0%, yeast extract 0.2%, glucose 1.0%, $(NH_4)_2HPO_4$ 0.05%, pH 6.0) were inoculated into a sterile 300 ml Erlenmeyer flask with the strain *Stachybotris atra* ST002348, DSM 14952 and incubated on a rotating shaker for 6 days at 25° C. and 140 rpm. 1.5 ml of this culture were then diluted with 2.5 ml of 50% strength glycerol and stored at −135° C.

EXAMPLE 2

Preparation of a Preculture in an Erlenmeyer Flask of *Stachybotris atra* ST002348, DSM 14952

A 300 ml Erlenmeyer flask with 100 ml of the following nutrient solution: malt extract 2.0%, yeast extract 0.2%, glucose 1.0%, $(NH_4)_2HPO_4$ 0.05%, pH 6.0, was inoculated with a culture grown on a slant tube/petri dish (same nutrient solution, but with 2% agar) or with 1 ml of a glycerol culture (see example 1) and incubated on a shaker at 140 rpm and 25° C.

EXAMPLE 3

Preparation of a Main Culture in an Erlenmeyer Flask of *Stachybotris atra* ST002348, DSM 14952

A 300 ml Erlenmeyer flask with 100 ml of the following nutrient solution: 0.5% soluble starch, 0.5% cornstarch, 1% glucose, 0.5% yeast extract, 0.5% "cornsteep" and 0.2% $CaCO_3$, was inoculated with 2 ml of a preculture (see example 2) and incubated on a shaker at 140 rpm and 25° C. The maximum production of one or more compounds of the spirobenzofuran lactam derivatives according to the invention is achieved after about 120 hours. For the inoculation of 10 l fermenters, a 48 to 96 hour-old submerse culture (inoculation amount about 10%) of the same nutrient solution sufficed.

EXAMPLE 4

Preparation of the Spirobenzofuran Lactam Derivatives

A 30 l fermenter was operated under the following conditions:

| | |
|---|---|
| nutrient medium: | 5 g/l of starch |
| | 5 g/l of cornstarch |
| | 5 g/l of cornsteep, liquid |
| | 5 g/l of yeast extract, |
| | 5 g/l of $CaCO_3$ |
| | pH 6.0 (before sterilization) |
| incubation time: | 96 hours |
| incubation temperature: | 25° C. |
| stirrer speed: | 150 rpm |
| aeration: | 15 l min$^{-1}$ |

By repeated addition of ethanolic polymer solution, it was possible to suppress foam formation. The production maximum was achieved after about 72 to 120 hours.

EXAMPLE 5

Isolation of the Spirobenzofuran Lactam Derivatives from the Shaker Cultures of *Stachybotris atra* ST002348, DSM 14952

After completion of the fermentation of *Stachybotris atra* ST002348, DSM 14952, the culture broth of 50 shaker flasks (in each case 100 ml of culture broth) was lyophilized together with the biomass and the lyophilizate was extracted with 2×5 liters of methanol. The active compound-containing, methanolic solution was freed from the residue by filtration and concentrated in vacuo. The concentrate was diluted with water and applied to a prepared 1.0 liter MCI GEL, CHP 20P column. It was eluted using a gradient of water to 100% acetonitrile in 60 minutes. The column eluate (30 ml per minute) was collected in fractions (30 ml each) and the fractions containing spirobenzofuran lactam derivatives (fr. 26–40) were combined. After concentration in vacuo and subsequent lyophilization, 2.9 g of a pale pink powder were isolated.

EXAMPLE 6

Preliminary Separation of the Spirobenzofuran Lactam Derivatives by RP 18 Chromatography About 1 g of the product obtained according to example 5 was applied to a LiChrospher® 100 RP-18 (e) column (size: 50 mm×250 mm; Merck, Darmstadt) and eluted using a gradient of 20% acetonitrile (+water with addition of 0.1% trifluoroacetic acid) to 90% acetonitrile with a flow rate of 45 ml per minute. The column eluate was collected in fractions (45 ml), spirobenzofuran lactam derivatives mainly being found in fractions 95 to 112. They were combined, freed from the solvent in vacuo and then lyophilized. The yield was 170 mg.

EXAMPLE 7

Purification of the Spirobenzofuran Lactam Derivatives 100 mg of the mixture isolated and concentrated according to example 6 were applied to a LUNA® 5μ C18(2) column (size: 21 mm×250 mm) and chromatographed using a gradient of 30 to 85% acetonitrile (+water with addition of 0.05% TFA). The flow of the eluant was 25 ml per minute, the fraction size 25 ml. Fraction 32 contained the compound of the formula (II) and afforded 6.1 mg after lyophilization. Fraction 33 contained the compound of the formula (III) and afforded 5.5 mg after lyophilization. Fraction 34 contained the compound (IV) and afforded 5.2 mg after lyophilization.

The physicochemical and spectroscopic properties of the substances according to the invention be summarized as follows:

EXAMPLE 8

Characterization of the Compound of the Formula (II)

| Empirical formula: | $C_{32}H_{39}NO_6$ |
|---|---|
| Molecular weight: | 533.67 |
| UV maxima: | 248, 348 |

TABLE 2

$^1$H and $^{13}$C chemical shifts of compound (II) in DMSO-$d_6$ at 300 K

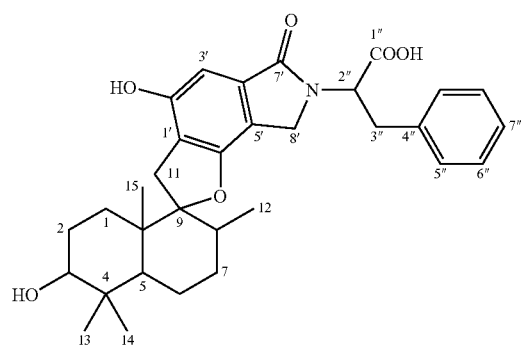

(II)

| | $^1$H | $^{13}$C[a] |
|---|---|---|
| 1 | 1.73/0.92 | 23.8 |
| 2 | 1.81/1.40 | 24.8 |
| 3 | 3.18 | 73.3 |
| 5 | 2.01 | 39.3 |
| 6 | 1.46/1.40 | 20.4 |
| 7 | 1.53/1.39 | 30.7 |
| 8 | 1.77 | 36.4 |
| 11 | 3.10/2.73 | 31.6 |
| 12 | 0.59 | 15.5 |
| 13 | 0.88 | 28.6 |
| 14 | 0.79 | 22.3 |
| 15 | 0.94 | 15.8 |
| 2'-OH | 9.68 | — |
| 3' | 6.49 | 100.8 |
| 8' | 4.26 | 44.3 |
| 2" | 5.11 | 54.5 |
| 3" | 3.33/3.27 | 34.4 |
| 5" | 7.22 | 128.2 |
| 6" | 7.25 | 128.4 |
| 7" | 7.14 | 126.4 |

[a] The values for the $^{13}$C chemical shifts are only given to one decimal place, since they were determined from the HMQC spectrum.

EXAMPLE 9

Characterization of the Compound of the Formula (III)

| Empirical formula: | $C_{29}H_{41}NO_6$ |
|---|---|
| Molecular weight: | 499.65 |
| UV maxima: | 248, 348 |

TABLE 3

$^1$H and $^{13}$C chemical shifts of compound (III) in DMSO-$d_6$ at 300 K

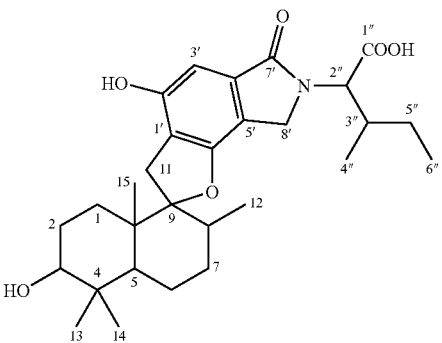

(III)

| | $^1$H | $^{13}$C[a] |
|---|---|---|
| 1 | 1.74/0.92 | 23.8 |
| 2 | 1.79/1.39 | 24.8 |
| 3 | 3.18 | 73.4 |
| 3-OH | 4.07 | — |
| 4 | — | 37.3 |
| 5 | 2.03 | 39.4 |
| 6 | 1.44 | 20.4 |
| 7 | 1.52/1.41 | 30.7 |
| 8 | 1.79 | 36.5 |
| 9 | — | 98.0 |
| 10 | — | 41.8 |
| 11 | 3.12/2.77 | 31.6 |
| 12 | 0.66 | 15.5 |
| 13 | 0.88 | 28.6 |
| 14 | 0.80 | 22.3 |
| 15 | 0.95 | 15.7 |
| 1' | — | 117.0 |
| 2' | — | 153.8 |
| 2'-OH | 9.73 | — |
| 3' | 6.58 | 100.9 |
| 4' | — | 132.8 |
| 5' | — | 112.2 |
| 6' | — | 155.8 |
| 7' | — | 167.9 |
| 8' | 4.39/4.28 | 44.2 |
| 1" | — | 172.1 |
| 2" | 4.55 | 58.3 |
| 3" | 2.12 | 33.8 |
| 4" | 0.96 | 15.7 |
| 5" | 1.31/1.05 | 25.1 |
| 6" | 0.84 | 10.3 |

[a] The values for the $^{13}$C chemical shifts are only given to one decimal place, since they were determined from the 2D spectra.

EXAMPLE 10

Characterization of the Compound of the Formula (IV)

| Empirical formula: | $C_{29}H_{41}NO_6$ |
|---|---|
| Molecular weight: | 499.65 |
| UV maxima: | 248, 348 |

TABLE 4

$^1H$ and $^{13}C$ chemical shifts of compound (IV) in DMSO-$d_6$ at 300 K

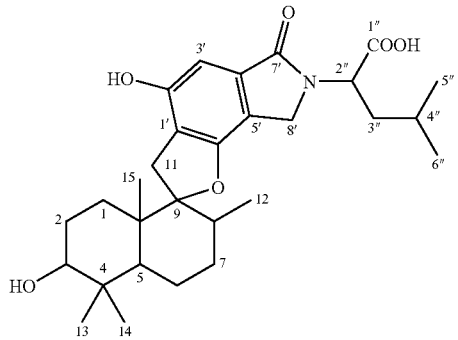

(IV)

| | $^1H$ | $^{13}C$ |
|---|---|---|
| 1 | 1.75/0.94 | 23.80 |
| 2 | 1.80/1.41 | 24.77 |
| 3 | 3.18 | 73.38 |
| 3-OH | 4.09 | — |
| 4 | — | 37.22 |
| 5 | 2.03 | 39.32 |
| 6 | 1.41 | 20.37 |
| 7 | 1.52/1.41 | 30.65 |
| 8 | 1.79 | 36.47 |
| 9 | — | 97.96 |
| 10 | — | 41.72 |
| 11 | 3.13/2.77 | 31.63 |
| 12 | 0.65 | 15.48 |
| 13 | 0.88 | 28.53 |
| 14 | 0.79 | 22.29 |
| 15 | 0.95 | 15.75 |
| 1' | — | 116.85 |
| 2' | — | 153.68 |
| 2'-OH | 9.72 | — |
| 3' | 6.58 | 100.83 |
| 4' | — | 133.12 |
| 5' | — | 112.22 |
| 6' | — | 155.85 |
| 7' | — | 168.03 |
| 8' | 4.30/4.25 | 43.77 |
| 1" | — | 173.03 |
| 2" | 4.81 | 51.50 |
| 3" | 1.98/1.70 | 37.41 |
| 4" | 1.40 | 24.50 |
| 5" | 0.91 | 22.82 |
| 6" | 0.87 | 20.78 |

EXAMPLE 11

Bioassay for PAI-1 Inhibitors

Reaction: The inhibition of the enzymatic activity of tPA by PAI-1 is measured by means of the amidolysis of the chromogenic substrate H-D-Ile-Pro-Arg-pNA (Chromogenix; pNA=para-nitroaniline) as the optical density (OD) at a wavelength of 405 nm.

Test Substances:

Extracts or pure substances, for example of the spirobenzofuran lactam derivatives prepared or characterized in examples 4–10, which are present dissolved in DMSO, were diluted in a suitable manner using TRIS buffer pH 8.4.

Method:

5 µl of test substance and 5 µl of PAI-1 are preincubated at room temperature for 30 minutes. 10 µl of tPA solution and 20 µl of substrate solution are then added.

The final concentrations in the sample are 50 µM test substance, 4.5 nM PAI-1, 7.5 nM tPA and 1 mM substrate in TRIS buffer pH 8.4. Immediately after the addition of the substrate, the initial absorption is measured at 405 nm. After incubation at 37° C. for 60 minutes, the absorption is measured again.

In each case, blank samples (buffer instead of tPA), positive controls=B (buffer instead of test substances) and tPA controls=A (buffer instead of PAI-1) are co-tested.

After correction by means of the blank samples, the inhibition is determined according to the following equation:

$$\% \text{ inhibition} = 100 - \frac{\Delta OD_{405nm} \text{ mean value } A - \Delta OD_{405nm} \text{ sample}}{\Delta OD_{405nm} \text{ mean value } A - \Delta OD_{405nm} \text{ mean value } B} \times 100$$

The results of the assay are shown as $IC_{50}$ values in Table 1.

What is claimed is:

1. A compound of the formula (I)

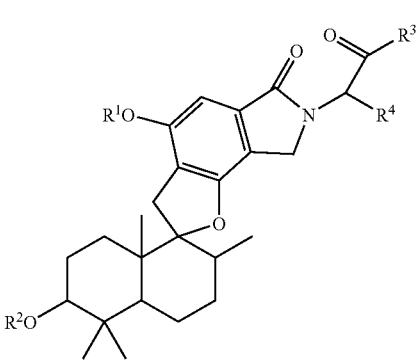

(I)

wherein $R^1$ and $R^2$ are H, $R^3$ is —$OR^1$ and $R^4$ is benzyl, 2-butyl, or 1-(2-methyl)-propyl, or a physiologically tolerable salt of the compound of the formula (I).

2. The compound according to claim 1 having the following formula (II)

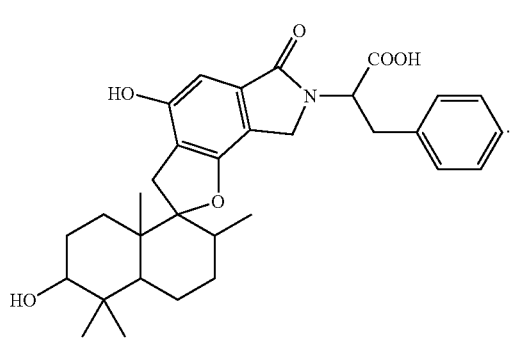
(II)

3. The compound according to claim 1 having the following formula (III)

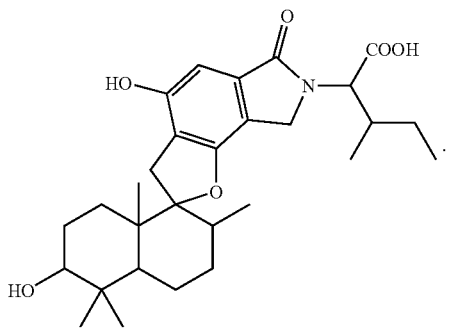
(III)

4. The compound according to claim 1 having the following formula (IV)

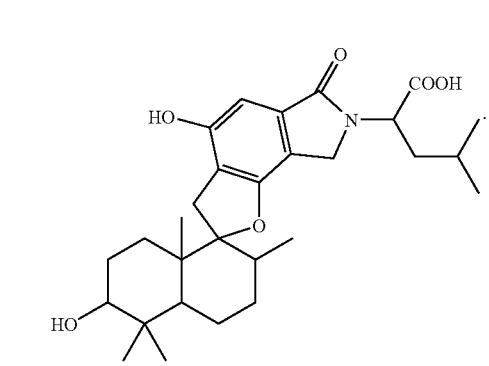
(IV)

5. A process for the preparation of a compound of the formula (I) as claimed in claim 1, which comprises fermenting the strain *Stachybotris atra* ST002348, DSM 14952, or one of its variants or mutants under suitable conditions in a culture medium until one or more of the compounds of the formula (I) accumulate in the culture medium and then isolating it from the culture medium and optionally converting it into a physiologically tolerable salt.

6. A pharmaceutical composition comprising a pharmaceutically effective amount of at least one compound of the formula (I) or of a physiologically tolerable salt thereof as claimed in claim 1, alone or as a mixture with one or more of the customary pharmacologically suitable vehicles or excipients.

* * * * *